United States Patent [19]

Parran, Jr. et al.

[11] Patent Number: 5,015,466

[45] Date of Patent: May 14, 1991

[54] ANTICALCULUS COMPOSITIONS USING TARTRATE-SUCCINATES

[75] Inventors: John J. Parran, Jr.; Margaret M. Coyle-Rees, both of Cincinnati; John T. Rotruck; Richard J. Sunberg, both of Oxford, all of Ohio

[73] Assignee: The Procter & Gamble Company, Cincinnati, Ohio

[21] Appl. No.: 543,647

[22] Filed: Jun. 26, 1990

[51] Int. Cl.$^5$ .......................... A61K 7/18; A61K 7/24
[52] U.S. Cl. .......................................... 424/52; 424/48; 424/55; 424/59; 424/435; 424/441; 426/3
[58] Field of Search .......................... 424/48, 49, 52, 55, 424/57, 435, 441; 426/3

[56] References Cited

U.S. PATENT DOCUMENTS

| | | | |
|---|---|---|---|
| 4,452,820 | 6/1984 | D'Amelia et al. | 426/3 |
| 4,582,709 | 4/1986 | Peters et al. | 426/74 |
| 4,663,071 | 5/1987 | Bush et al. | 252/174.19 |
| 4,689,167 | 8/1987 | Collins et al. | 252/95 |
| 4,721,580 | 1/1988 | Gosselink | 252/90 |
| 4,877,896 | 10/1989 | Maldonado et al. | 560/14 |
| 4,904,824 | 2/1990 | Horng et al. | 562/583 |
| 4,925,586 | 5/1990 | Baker et al. | 252/90 |
| 4,959,409 | 9/1990 | Heinzman et al. | 525/61 |
| 4,968,451 | 11/1990 | Scheibel et al. | 252/549 |

Primary Examiner—Shep K. Nose
Attorney, Agent, or Firm—Jerry J. Yetter; Richard C. Witte; Douglas C. Mohl

[57] ABSTRACT

Tartrate monosuccinate and tartrate disuccinate compounds of the formulas HO(CHCOOX)CH(COOX)OCH(COOX)CH$_2$COOX and CH$_2$(COOX)CH(COOX)O(CH[COOX])$_2$OCH(COOX)CH$_2$COOX are used to provide anticalculus benefits on teeth. Oral care composition such as dentifrices, mouthwashes, and the like, are provided. Use of the tartrate-succinates in combination with other oral care ingredients such as fluoride, pyrophosphate and antibactrials is also described.

31 Claims, No Drawings

ANTICALCULUS COMPOSITIONS USING TARTRATE-SUCCINATES

TECHNICAL FIELD

The present invention relates to oral care compositions such as dentifrices, mouthwashes, lozenges, chewing gums, and the like, which are designed to prevent the accumulation of calculus, or "tartar", as it is sometimes called, on teeth.

1. Background of the Invention

Dental calculus is a deposit which forms on the surfaces of the teeth at the gingival margin. Supragingival calculus appears principally in the areas near the orifices of the salivary ducts; e.g., on the lingual surfaces of the lower anterior teeth and on the buccal surfaces of the upper first and second molars, and on the distal surfaces of the posterior molars.

Mature calculus consists of an inorganic material which is largely calcium phosphate arranged in a hydroxyapatite crystal lattice structure similar to bone, enamel and dentine. An organic portion is also present and consists of desquamated epithelial cells, leukocytes, salivary sediment, food debris and various types of microorganisms.

As the mature calculus develops, it becomes visibly white or yellowish in color unless stained or discolored by some extraneous agent. In addition to being unsightly and undesirable from an aesthetic standpoint, the mature calculus deposits are constant sources of irritation of the gingiva.

A wide variety of chemical and biological agents have been suggested in the art to retard calculus formation or to remove calculus after it is formed. Mechanical removal of this material periodically by the dentist is, of course, routine dental office procedure.

The chemical approach to calculus inhibition generally involves chelation of calcium ion and/or crystal growth inhibition which prevents the calculus from forming and/or breaks down mature calculus by removing calcium.

U.S. Pat. No. 4,885,155, to Parran and Sakkab, granted Dec. 5, 1989, relates to oral compositions containing pyrophosphate salts which provide an anticalculus benefit.

As will be seen hereinafter from the discussion of the literature, there has been a continuing search for anticalculus agents. Unfortunately, the chemical composition of calculus is sufficiently similar to that of the healthy tooth mineral (primarily, calcium hydroxyapatite) that many materials which can attack and remove calculus would also undesirably attack the underlying tooth structure. This is particularly true with regard to many chelating agents which sequester calcium ions. Accordingly, while materials such as the pyrophosphates of U.S. Pat. No. 4,885,155, above, are used to prevent calculus formation on teeth, there has been a continuing search for materials which can safely remove calculus from teeth and/or effectively prevent its build-up.

The present invention provides a new solution to the problem of dental calculus by means of the tartrate/succinate compositions disclosed hereinafter.

2. Background Art

The synthesis of tartrate monosuccinate and tartrate disuccinate compounds of the type used in the practice of this invention is disclosed in U.S. Pat. No. 4,663,071, to Bush, Connor, Heinzman and Mackey, granted May 5, 1987.

Various references in addition to U.S. Pat. No. 4,885,155, cited above, relate to anticalculus agents of various types. The prior art discloses a number of chelating agents for this purpose. British Patent No. 490,384, Feb. 15, 1937, discloses oral compositions containing ethylenediaminetetraacetic acid, nitrilotriacetic acid and related compounds as anticalculus agents. This patent goes on to say:

> ... other substances displaying a tartar dissolving action may be present in the tooth cleansing agent according to our present invention. As such additional ingredient we prefer the water soluble metaphosphates or pyrophosphates. In this connection there may be mentioned by way of example the alkali metal salts of these phosphates, especially sodium hexametaphosphate which may for instance be prepared by heating primary phosphates with subsequent rapid cooling of the melt. Also the water soluble salts of pyrophosphoric acids, for instance the secondary and quaternary alkali metal salts such as the sodium, potassium, lithium and ammonium salts and also the salts of certain basic organic compounds such as amines may be used.

U.S. Pat. No. 3,678,154, July 18, 1972 to Widder, et al. discloses oral compositions containing certain polyphosphonates and fluoride. U.S. Pat. No. 3,737,533, June 5, 1973 to Francis discloses oral compositions containing certain carbonyl diphosphonates.

In addition to the above references, the prior art discloses dentifrices and mouthwashes containing soluble pyrophosphate salts which have been indicated for a variety of purposes. Included among such references are U.S. Pat. No. 2,941,926, June 21, 1960 to Salzmann, et al. which discloses dental powders containing chlorophyll and pyrophosphate salts. U.S. Pat. No. 3,137,632, June 16, 1964 to Schiraldi discloses toothpastes containing pyrophosphate salts. U.S. Pat. Nos. 3,927,201 and 3,927,202, Dec. 16, 1975 to Baines, et al. and Harvey, et al., respectively, disclose toothpastes which utilize soluble pyrophosphates as abrasives. U.S. Pat. Nos. 4,244,931, Jan. 13, 1981 and 4,247,5226, Jan. 27, 1981 to Jarvis, et al. disclose pyrophosphate salts in dicalcium phosphate systems. Japanese Patent Application Disclosure No. 4945-1974 discloses soluble pyrophosphates in a variety of dentifrice systems. U.S. Pat. No. 4,333,551, Apr. 6, 1982 to Parran discloses tetraalkali metal salts in mouthwash compositions. Draus, Lesniewski and Miklos, *Pyrophosphate and Hexametaphosphate Effects In Vitro Calculus Formation*, Arch. Oral Biol., Vol. 15, pp. 893-896 (1970), disclose the in vitro effectiveness of soluble pyrophosphate salts against calculus. However, they indicate that pyrophosphate efficacy would be inhibited by phosphatases in vivo.

The references suggesting that pyrophosphates could reduce calculus, but either suggesting problems associated with their use or not recognizing problems, are Rapp, G. W. et al, "Pyrophosphate: a factor in Tooth Erosion", J. D. Res. March-April 1960, Vol. 39, No. 2 pp. 372-376; the Draus article cited above; Briner et al, "In Vitro and In Vivo Evaluation of Anticalculus Agents", *Calc. Tiss.* 11, pp. 10-22 (1973); U.S. Pat. No. 3,934,002, Jan. 20, 1976 to Haefele; and British Patent No. 490,384, Feb. 15, 1937.

U.S. Pat. No. 4,847,070, July 11, 1989 to Pyrz et al. relates to oral compositions which are effective against calculus containing a chelating agent which is an acrylic acid polymer or copolymer or EDTA, together with a strontium source, a fluoride ion source and a pyrophosphate ion source.

U.S. Pat. No. 4,661,341, Apr. 28, 1987 to Benedict et al. relates to oral compositions containing an anticalculus agent which is an acrylic acid polymer or copolymer.

U.S. Pat. No. 4,022,880, May 10, 1977 to Vinson et al. relates to compositions for inhibiting dental plaque and calculus formation comprising zinc ions and a nontoxic, organoleptically acceptable antibacterial agent.

U.K. Patent Application GB 2,200,551, Gaffar, Nabi and Jannone, filed Jan. 27, 1988, published Aug. 10, 1988, relates to antibacterial, antiplaque and anticalculus oral compositions containing a linear molecularly dehydrated polyphosphate salt and a noncationic antibacterial agent.

U.S. Pat. No. 4,656,031, Apr. 7, 1987 to Lane et al. relates to a dentifrice which includes a surfactant and an antiplaque agent comprising a substantially water-insoluble noncationic antimicrobial agent or a zinc salt or a mixture thereof.

European Patent Application 0,251,591, Jackson et al., filed June 19, 1987 relates to oral hygiene compositions comprising specified pyrophosphates and antibacterials.

As noted above, U.S. Pat. No. 4,885,155, Dec. 5, 1989 to Parran, Jr. et al. relates to oral compositions containing particular pyrophosphate salts which provide an anticalculus benefit.

SUMMARY OF THE INVENTION

The present invention encompasses oral care composition comprising an effective amount of an anticalculus agent which is a member selected from the group consisting of the acid or salt form of tartrate monosuccinate, tartrate disuccinate, and mixtures thereof, and a toxicologically acceptable oral carrier. Preferred compositions herein comprise at least about 0.1% by weight of said anticalculus agent, and most preferably comprise from about 1% to about 15% by weight of said anticalculus agent.

Preferred compositions according to this invention are those wherein said anticalculus agent is a mixture of said tartrate monosuccinate and tartrate dissuccinate at a weight ratio of tartrate monosuccinate:tartrate disuccinate from about 20:80 to about 80:20, preferably at a weight ratio of about 40:60.

Compositions provided by this invention are those wherein said oral carrier is, for example, a dentifrice (including gels, powders, pastes, and the like), mouthwashes, lozenges, or the like, chewing gum, and the like.

Highly preferred oral care compositions according to this invention additionally comprise a source of an effective amount of fluoride ions. Such sources can include, for example, sodium fluoride, stannous fluoride, sodium monofluorophosphate, and the like. Said source of fluoride ions typically comprises from about 0.01% to about 1% by weight of the compositions herein. Dentifrice and mouthwash compositions containing the tartrate monosuccinate, tartrate disuccinate or mixtures thereof with fluoride sources are exemplified hereinafter.

The oral care compositions according to this invention can additionally comprise an effective amount of an antibacterial agent, e.g., as an antiplaque agent and/or antigingivitis agent. Antibacterials such as TRICLOSAN and Cetyl Pyridinium Chloride (CPC) are especially useful. Such compositions can also additionally comprise a source of an effective amount of fluoride ions. (TRICLOSAN is the trade name for 5-chloro-2-(2,4-dichlorophenoxy)-phenol, also known as 2,4,4'-trichloro-2'-hydroxydiphenyl ether; see U.S. Pat. No. 3,506,720.

Moreover, the oral care compositions according to this invention can also additionally comprise an effective amount of a source of pyrophosphate ions to provide additional calculus-controlling benefits, and such compositions can also additionally comprise a source of an effective amount of fluoride ions, and/or an effective amount of an antibacterial agent, such as those noted above.

In addition, oral care compositions herein can additionally comprise an effective amount of zinc citrate as an adjunct calculus-controlling agent.

A typical oral care composition herein in the form of a dentifrice, comprises:

from about 15% to about 30% by weight of an abrasive;
  from about 0.1% to about 15% by weight of an anticalculus agent which comprises a mixture of tartrate monosuccinate and tartrate disuccinate, preferably at a weight ratio of tartrate monosuccinate:tartrate disuccinate of about 40:60; and
  from about 0.05% to about 0.5% by weight of a source of fluoride ions.

Still other oral care compositions according to this invention can additionally comprise an effective amount of a source of a cation selected from the group consisting of zinc, indium, strontium and stannous cations, and mixtures thereof. Such compositions, or compositions which additionally comprise an effective amount of a member selected from the group consisting of sodium nitrate and potassium nitrate, are useful when treating sensitive teeth, e.g., in older patients.

The invention also encompasses a method for preventing the accumulation of calculus on dental enamel comprising contacting said dental enamel with a safe and effective amount of tartrate monosuccinate anion, tartrate disuccinate anion, or mixtures thereof. Preferably, this method employs a mixture of said tartrate monosuccinate and disuccinate anions and is employed on a daily basis, e.g., by brushing the calculus-prone teeth, especially in the presence of an acceptable abrasive, or by rinsing with a mouthwash. Preferably, this procedure is carried out in the presence of a member selected from the group consisting of sources of fluoride ions. This procedure can also be carried out in conjunction with the use of adjunct agents, as noted herein, such as antibacterial agents, a source of pyrophosphate ions, a metal cation selected from the group consisting of zinc, indium, strontium and stannous cations, sodium nitrate, potassium nitrate, or mixtures thereof.

Of course, since the compositions herein are intended for oral use, toxicologically-acceptable materials are used in the various compositions and methods disclosed hereinafter.

All percentages, weights, ratios and proportions herein are by weight, unless otherwise specified.

DETAILED DESCRIPTION OF THE INVENTION

The present invention employs tartrate monosuccinate and tartrate disuccinate materials of the following formulae:

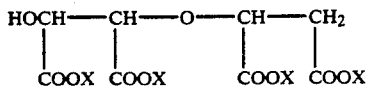

i.e., tartrate monosuccinate, otherwise designated "TMS"; and

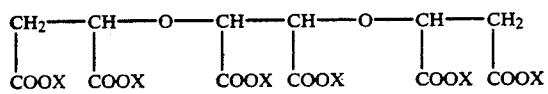

i.e., tartrate disuccinate, otherwise designated "TDS", and wherein X in the above formulae can be, for example, H or a salt-forming cation, especially cations which form water-soluble salts, e.g., alkali metal, ammonium, alkylammonium, alkanolammonium, and the like. Sodium and potassium cations are conveniently and economically used to form salts of TMS and TDS for use in this invention.

The TMS and TDS materials can be prepared using the procedures disclosed in U.S. Pat. No. 4,663,071, cited above, using maleates and tartrates in whatever isomeric forms are convenient to the formulator, e.g., D-, L- or DL stereoisomers of tartaric acid. In general, mixtures of TMS and TDS are secured, which, if desired, can be separated into their individual components, e.g., by HPLC. As noted, mixtures of TMS and TDS are acceptable for use herein.

Reaction A—An alternate mode for preparing mixtures of TMS/TDS having a desirably higher proportion of TDS is as follows. The reaction illustrated employs water (122 g.), 50% aq. NaOH (608 g.), L-tartaric acid (150 g.), Ca(OH)$_2$ (118 g.) and maleic anhydride (392 g.).

The water is added to the reaction vessel which is placed in a water bath at 60° C. The NaOH is added with slow stirring. The L-tartaric acid is added slowly and allowed to dissolve. The exotherm is maintained at 60°-80° C. Slowly add the Ca(OH)$_2$ to form a milky suspension. Maleic anhydride is slowly added while keeping the reaction temperature $\leq 85°$ C. The mixture is allowed to react at 70°-80° C. for 1 hour during which time it will turn from a chalky white suspension to a honey colored viscous reaction mixture. After 1 hour, the reaction temperature is lowered to 30° C. and maintained for a total reaction duration of 9-10 days. The reaction concentration is maintained at 60% sodium organic salts. The reaction is monitored by HPLC to determine the optimum yield (Stir the reaction about 0.5 hour before sampling.) When the yield of TMS+TDS approaches a plateau, the reaction is quenched with ca. 1400 g H$_2$O and by removing the calcium.

Calcium removal is as follows. Heat the reaction solution to 70° C. with stirring. Slowly add 161 g Na$_2$CO$_3$ followed by 31.9 g of NaHCO$_3$. Rinse with extra H$_2$O if needed. Stir the mixture at 70° C., pH 10, for 4 hours. After 4 hours, cool to $\leq 35°$ C. and filter through coarse fritted filters. Rinse with minimal H$_2$O.

Acid workup is as follows. Add about 450 g of 50% H$_2$SO$_4$ to the "calcium free" solution to pH 4 with stirring to precipitate the residual maleate. Maintain the exotherm at $\leq 50°$ C. Let the solution sit overnight to enhance crystallization. Filter through coarse fritted filters via vacuum filter flasks. Use no rinse. Slowly add 160 g of 50% NaOH to the filtrate to pH 9 with stirring. Maintain the exotherm at $\leq 50°$ C. Concentrate the solution to about half the current volume (to precipitate Na$_2$SO$_4$) and let sit overnight to enhance crystallization. Filter off the Na$_2$SO$_4$ through coarse fritted filters via vacuum filter flasks. Repeat the evaporation and filtration as often as necessary to remove residual Na$_2$SO$_4$.

Workup in alcohol is as follows. Slowly pour the reaction solution ($\sim 40\%$ concentration) into 8.8 L of stirring methanol (MeOH) to remove residual maleate, fumarate, carbonate, and sulfate. The TMS/TDS will precipitate out on the bottom of the vessel as a sticky "gum", while the impurities will remain in the MeOH/H$_2$O layer. Decant/Siphon off as much of the MeOH/H$_2$O as possible and discard. Redissolve the TMS/TDS with 1.6 L H$_2$O using heat and stirring as necessary. Cool to $\leq 35°$ C. and repeat with a second extraction. Pour the solution into 6.4 L of stirring MeOH. Again decant/siphon off as much of the MeOH/H$_2$O as possible and discard. Redissolve the TMS/TDS in 1.4 L water and repeat as before, using 5.6 L methanol. Redissolve the TMS/TDS in ca. 1 L H$_2$O. It is now ready for the final workup.

Final workup is as follows. Adjust the reaction solution to about pH 8.5 at 24° C. Heat to ca. 80° C. with stirring and nitrogen sparging to remove residual traces of MeOH. Concentrate the solution to 35% sodium organic salts. Cool to room temperature. Adjust the solution to the desired pH. Add H$_2$O to adjust the final concentration if necessary. Filter through medium fritted filters.

Reaction B—Another, somewhat simpler, procedure which can be employed to prepare TMS/TDS mixtures comprising a higher ratio of TDS to TMS is as follows. The reaction illustrated employs water (86 g.), 50% NaOH (336 g.), L-tartaric acid (150 g.), Ca(OH)$_2$ (89 g.) and maleic anhydride (196 g.).

Add H$_2$O to the reaction vessel which is placed in a water bath at 60° C. Add the NaOH with slow stirring. Slowly add the L-tartaric acid and let dissolve. Maintain the exotherm at 60°-80° C. Slowly add Ca(OH)$_2$ which will form a milky suspension. Slowly add maleic anhydride while keeping the reaction temperature $\leq 85°$ C. Allow the mixture to react at 70°-80° C. for 1 hour during which time it will turn from a chalky white suspension to a honey colored viscous reaction mixture. After 1 hour, lower the reaction temperature to 30° C. and maintain it for a total reaction duration of 9-10 days. Maintain the reaction concentration at 60% sodium organic salts. Monitor the reaction by HPLC to determine the optimum yield. (Stir the reaction mixture about 0.5 hour before sampling.) When the yield of TMS+TDS approaches a plateau, proceed by quenching the reaction with ca. 850 g. H$_2$O and by removing the calcium.

Calcium removal is as follows. Heat the reaction solution to 70° C. with stirring. Slowly add 121.9 g. Na$_2$CO$_3$ followed by 24.4 g. NaHCO$_3$ to form a milky suspension. The mole ratio of carbonate to calcium is 1.2 carbonate to 1.0 calcium. Adjust the pH of the suspension to 10.0 at 70° C. with additional Na$_2$CO$_3$ or NaHCO₃ if needed. Rinse with extra H₂O if needed. Stir the mixture at 70° C., pH 10, for 4 hours. After 4 hours, cool to ≦35° C. and filter through coarse fritted filters. Rinse with minimal H₂O.

Workup with methanol (MeOH) is optional. If methanol workup is used, the procedure is the same as in Reaction A, above.

Final workup is as follows. If a MeOH workup is used, adjust the reaction solution to about pH 8.5 at 24° C. Heat to ca. 80° C. with stirring and nitrogen sparging to remove residual traces of MeOH. Concentrate the solution to 35% sodium organic salts. Cool to room temperature. Adjust the solution to the desired pH. Add H₂O to adjust the final concentration if necessary. Filter through medium fritted filters.

Having thus described procedures useful for preparing TMS, TDS, and TMS/TDS compounds and mixtures of the type employed herein, the use of such materials to prepare oral care compositions and the use of such compositions in an oral care regimen are disclosed hereinafter.

It is to be understood that the compositions and processes herein are designed to deliver an effective amount of the functional ingredients such as TMS, TDS, fluoride, antibacterial agent, and the like, to the oral cavity safely and conveniently so that the desired anticalculus benefits are achieved. For most purposes, contacting the teeth which are prone to calculus accumulation with the TMS, TDS and/or mixed TMS/TDS anions for a period of from about 10 seconds to about 3 minutes once, or preferably three times, daily in an otherwise conventional oral care regimen of tooth brushing and/or use of mouthwash, will provide the desired benefits. Lesser or greater degrees of anticalculus benefits can be achieved by modifying the regimen. For example, use of a lozenge or chewing gum containing the TMS and TDS materials provides prolonged contact of the teeth with the active anions.

The formulation of oral care compositions using TMS and TDS in the manner of this invention employs otherwise conventional ingredients such as well-known dentifrice abrasives, flavorants, thickening agents, fluid carriers (especially water-ethanol), sweetening agents, especially noncariogenic sweeteners such as the aspartic acid-derived sweeteners, saccharin and/or cyclamate, standard dental grade sources of fluoride ions such as sodium fluoride, stannous fluoride, and sodium monofluorophosphate (which are noted herein by way of exemplification, and not by way of limitation) and like materials which have come into broad usage in the dental arts. Various formularies are available and can be referred to for details of such materials.

As a typical example, the oral care compositions of this invention can comprise an effective amount of fluoride ions. By "effective amount" is meant sufficient fluoride ions to provide a dental enamel-strengthening effect which not only translates into an anticaries effect, but also which provides additional protection for the healthy dental enamel against the calcium sequestering action of the TMS and TDS anions. Typically, compositions comprising from about 0.0025% to about 2%, preferably from about 0.01% to about 1% by weight of said fluoride ion source will provide sufficient fluoride ions for these desired benefits.

By an "effective amount" of an antibacterial agent herein is meant sufficient antibacterial to provide an antiplaque benefit for the compositions. Typically, from about 0.001% to about 1% by weight of the compositions can comprise the desired antibacterial (antiplaque) amount. Preferred antibacterial agents for use herein include, for example, TRICLOSAN, CPC, PAM (magnesium monoperphthalate; see U.S. Pat. No. 4,670,252), TDEPC (N-tetradecyl-4-ethylpyridinium chloride) and sodium peroxide; TRICLOSAN is especially preferred.

By an "effective amount" of a source of pyrophosphate ions herein is meant an amount which will provide adjunct anticalculus benefits, in addition to those provided by the TMS and TDS anions. Typically, compositions will comprise from about 0.1% to about 10% by weight of pyrophosphate ions, which can be sourced from pyrophosphate salt such as tetrasodium, tetrapotassium, and disodium dihydrogen pyrophosphates.

By an "effective amount" of zinc citrate herein is meant an amount sufficient to provide adjunct anticalculus benefits in addition to those provided by the TMS and TDS anions. Typically, an amount of zinc citrate of from about 0.1% to about 5% by weight of the compositions herein is sufficient.

By an "effective amount" of a source of cation, especially cations selected from zinc, indium, strontium and stannous cations, and mixtures thereof, herein is meant a sufficient amount of said cations to provide the benefits which are normally associated with the use of these particular materials in oral compositions. For example, the stannous cation has been associated with an anticaries benefit, as has the indium cation. Zinc and strontium cations have been noted for use in, for example, dentifrice compositions which are used in situations where the teeth have been made "sensitive" to pain, particularly in older teeth which have undergone serious erosion of the dental enamel. Typical usage levels to provide the aforesaid effective amount of such cations generally ranges from about 0.01% to about 3% by weight of the compositions. Materials such as indium chloride, stannous fluoride, strontium chloride, zinc chloride, and the like can be used for such purposes.

By an "effective amount" of sodium nitrate and potassium nitrate (preferred) herein is meant sufficient amounts of such materials to provide desensitization of otherwise sensitive teeth (as noted above). Typically, such amounts will comprise from about 0.01% to about 5% of the compositions herein.

While not intending to be limited by theory, it appears that the TMS/TDS interacts with calculus precursor mineral substance, possibly in the form of amorphous calcium phosphate, thereby preventing the accumulation of mature, hard-to-remove calculus on the teeth. The method for preventing the accumulation of calculus on dental enamel herein comprises contacting said dental enamel with a "safe and effective" amount of the TMS, TDS, or mixtures thereof, typically in anion form, and the compositions herein are formulated to deliver such amounts. By "safe and effective" amount in this context is meant an amount sufficient to provide the intended benefit within the dosage regimen selected, as noted above. The amounts used can also be varied, according to the desires of the formulator, depending on the degree of calculus affliction suffered by the user. Typically, it is preferred that the teeth be "bathed" in a solution comprising from about 1000 ppm to about 100,000 ppm by weight of the anions for a period of 1–3 minutes at least once, preferably three times, daily, on a regular basis. Greater amounts can be used, as noted above. Usage can be assisted by brushing said dental enamel, preferably in combination with an abrasive, e.g., in a typical dentifrice formulation.

It will be appreciated by the formulator that it is desirable to use formulations wherein the TMS and TDS anions are substantially stable. Since these materials, particularly in their sodium salt form, are easily dissolved in water and water/alcohol, the formulation of mouthwashes presents no particular problem. The formulation of toothpastes likewise can employ materials which are well-known, and thickeners such as various gums and mucilages; abrasives such as silica and the various other polishing agents, and the like, well-known in the dental arts can be employed. Representative, but nonlimiting, examples of such materials are described in the formulations disclosed hereinafter.

Representative examples of abrasives useful herein include calcium carbonate, hydrated alumina, $\beta$-phase calcium pyrophosphate, urea-formaldehyde resins (see U.S. Pat. No. 3,070,510) and, as noted, the silica abrasives (see U.S. Pat. Nos. 3,538,230 and 3,862,307). "Syloid" silica xerogels, available from W. R. Grace and Company and precipitated silicas, e.g., "Zeodent 119" from J. M. Humber Corporation are a preferred class of abrasives used herein. Abrasives are typically in the 0.1 to 30 micron size, and are typically used in toothpastes at the 6% to about 80% level and in toothpowders at levels up to 99%. Silica abrasives are preferred herein.

Another embodiment of the present invention is a mouthwash composition. Conventional mouthwash compositions components can comprise the carrier for the actives of the present invention. Mouthwashes generally comprise from about 20:1 to about 2:1 of a water-/ethyl alcohol solution and preferably other ingredients such as flavoring agents, sweeteners, humectants and sudsing agents such as those described above. The humectants, such as glycerin and sorbitol, give a moist feel to the mouth. Generally, on a weight basis the mouthwashes of the invention comprise from about 5% to about 60%, preferably from about 10% to about 25%, of ethyl alcohol; from 0% to about 20%, preferably from about 5% to about 20%, of a humectant, from 0% to about 2%, preferably from about 0.01% to about 0.15%, of an emulsifying agent; from 0% to about 0.5% of a sweetening agent; from about 0.03% to about 0.3% of a flavoring agent; and from about 1% to about 10% of TMS or TDS.

Likewise, the formulation of chewing gums and lozenges presents no particular difficulties so long as toxicologically-acceptable carriers are used, as would naturally be the case in any product used in the oral cavity where ingestion of various ingredients by the user might occur. Suitable lozenge and chewing gum components are disclosed in U.S. Pat. No. 4,083,955, issued Apr. 11, 1978 to Grabenstetter et al. Suitable topical dental gels generally comprise a base of a humectant such as glycerin thickened with a suitable agent. Such gels generally do not contain an abrasive.

Flavoring agents can also be added to the compositions of the present invention. Suitable flavoring agents include oil of wintergreen, oil of peppermint, oil of spearmint, oil of sassafras and oil of clove. Sweetening agents are also useful and include aspartame, acesulfame, saccharin, dextrose, levulose and sodium cyclamate. Flavoring and sweetening agents are generally used in the compositions herein at levels of from about 0.005% to about 2% by weight.

The compositions of this invention may also contain emulsifying agents. Suitable emulsifying agents are those which are reasonably stable and foam throughout a wide pH range, and include non-soap anionic, non-ionic, cationic, zwitterionic and amphoteric organic synthetic detergents. Many of these suitable surfactants are disclosed by Gieske et al. in U.S. Pat. No. 4,051,234, issued Sept. 27, 1977, which is incorporated herein by reference.

Water may also be present in the compositions of this invention. Water employed in the preparation of commercially suitable compositions should preferably be deionized and free of organic impurities. Water generally comprises from about 10% to about 50% by weight, preferably from about 20% to about 40% by weight, of the toothpaste compositions herein. These amounts of water include the free water which is added plus that which is introduced with other materials, such as with sorbitol.

In preparing toothpastes, it is common to add some thickening material to provide a desirable consistency. Preferred thickening agents are carboxyvinyl polymers, carrageenan, hydroxyethyl cellulose and water soluble salts of cellulose ethers such as sodium carboxymethyl cellulose and sodium carboxymethyl hydroxyethyl cellulose. Natural gums such as gum karaya, gum arabic and gum tragacanth, and polysaccharide gums such as xanthan gum can also be used. Colloidal magnesium aluminum silicate or finely divided silica can be used as part of the thickening agent to further improve texture. Thickening agents in an amount from about 0.5% to about 5.0% by weight of the total composition may be used.

It is also desirable to include a humectant in a toothpaste to keep it from hardening. Suitable humectants include glycerin, sorbitol and other edible polyhydric alcohols at a level of from about 10% to about 70% by weight.

The pH of the present compositions and/or their pH in the mouth can be any pH which is safe for the mouth's hard and soft tissues. Such pH's are generally from about 3 to about 10, preferably from about 7 to about 9.

The following Examples further illustrate the practice of this invention, and describe typical formulations employing safe and effective amounts of the TMS/TDS, as well as various adjunct oral care ingredients encompassed by this invention and their uses, but are not intended to be limiting thereof.

EXAMPLE I

A toothpaste composition containing 5% anion from a TDS/TMS mixture is as follows.

| Ingredient | Percent (wt.) |
| --- | --- |
| Water (deionized) | 14.371 |
| Sorbitol | 24.654 |
| TDS/TMS mixture (40/60 25.7% anion) | 19.233 |
| NaF | 0.243 |
| NaSaccharin | 0.455 |
| Polyethylene glycol | 2.970 |
| 10 Mol/L NaOH | 0.970 |
| TiO$_2$ | 0.495 |
| FD&C Blue #1 | 0.0495 |
| Silica | 21.780 |
| Glycerin | 8.910 |
| Xanthan gum | 0.594 |
| Carbopol | 0.198 |
| Flavor | 1.089 |
| Sodium alkyl sulfate (27.9% aqueous solution) | 3.960 |

EXAMPLE II

A mouthwash composition containing 2% anion from a TDS/TMS mixture is as follows.

| Ingredient | Percent (wt.) |
| --- | --- |
| EtOH (190) by wt. | 8.500 |
| Sorbitol (70% aqueous solution) | 18.000 |
| TDS/TMS mixture (40/60 - aqueous solution 25.7% anion) | 7.800 |
| Polysorbate 80 | 0.600 |
| Dye (2% aqueous solution) | 0.070 |
| Pluronic F127 | 0.200 |
| Flavor | 0.075 |
| NaSaccharin | 0.040 |
| Sodium fluoride | 0.050 |
| 50% NaOH | to pH 7 |
| Water | Balance |

EXAMPLE III

A toothpowder composition is prepared by dry-blending ingredients, as follows:

| Ingredient | Percent (wt.) |
| --- | --- |
| Silica xerogel (9 micron) | 90.0 |
| Tartrate disuccinate, Na | 7.75 |
| Cetyl pyridinium chloride | 0.25 |
| Flavorant | 1.0 |
| Sodium alkyl sulfate | 1.0 |

EXAMPLE IV

A toothpaste composition is prepared according to Example I, but with the addition of 0.5% by weight of TRICLOSAN in place of an equivalent weight of abrasive. The resulting formulation provides anticalculus, antiplaque and anticaries benefits.

EXAMPLE V

A lozenge comprising 80% maltose, 5% tartrate monosuccinate (K salt), 1% sodium monofluorophosphate, 1.5% gum arabic, 0.1% strontium chloride, 0.1% flavorant, 0.05% magnesium stearate (tableting aid), the balance comprising corn starch, is prepared in a standard tablet press. In use, the lozenge is allowed to dissolve slowly in the mouth to bathe the teeth in the combination of active ingredients.

EXAMPLE VI

A chewing gum comprises 99.4% standard chewing gum base (chicle), 0.5% flavorant and 0.1% of the mixture of TDS/TMS prepared according to Reaction A, hereinabove.

EXAMPLE VII

A dentifrice powder comprises the following mixture of ingredients.

| Ingredient | Percent (wt.) |
| --- | --- |
| TDS/TMS (per Reaction B) | 5.0 |
| Silica xerogel (as "Syloid") | 90.0 |
| Tetrasodium pyrophosphate | 4.0 |
| Sodium fluoride | 1.0 |

The composition of Example VII can be modified by replacing the tetrasodium pyrophosphate with an equivalent amount of tetrapotassium pyrophosphate.

EXAMPLE VIII

A mild toothpowder for sensitive teeth comprises 90% $\beta$-calcium pyrophosphate abrasive, 0.2% stannous fluoride, 0.1% potassium nitrate, 0.15% zinc sulfate, 9% TDS/TMS (per Reaction B, herein), the balance comprising flavorant.

EXAMPLE IX

An oral gel dentifrice comprises 15% TMS/TDS (per Reaction A), 1.5% Veegum, 1.5% carboxymethyl cellulose, 1.0% NaF, the balance comprising water.

EXAMPLE X

Base toothpaste compositions comprising standard amounts and types of abrasives, thickeners, humectants, surfactants and flavorants and prepared and blended with the following combinations of ingredients to provide dentifrice compositions A through E as follows.

| Ingredient (wt. ratio) | Percent (wt.) in Dentifrice |
| --- | --- |
| A. Zinc citrate/TDS (0.1:1) | 10 |
| B. KF/PAM/TDEPC/TMS (1:0.1:0.1:10) | 15 |
| C. Sodium peroxide/TMS (1:1) | 5 |
| D. Indium trichloride/TDS/TMS (0.2:1:1) | 5 |
| E. TRICLOSAN/tetrasodium pyrophosphate/TMS (0.5:1:1) | 10 |

While the foregoing illustrates not only the use of the basic compositions of this invention and several embodiments thereof, but also various combinations of the herein-disclosed active ingredients with various adjunct agents for oral care, it is to be understood that such adjunct agents are given by way of exemplification and not by way of limitation. Other adjunct oral care agents can be used in such compositions, including materials such as: the ethylenediamine tetraacetates (EDTA) and the diphosphonates, especially ethane-1-hydroxy-1,1-diphosphonate (EHDP), (EHDP and EDTA generally at effective levels of 0.1%, or less); peroxides, especially 1% aqueous hydrogen peroxide; sodium tripolyphosphate (STPP), typically at 0.5%-10% levels, and the like. The following examples provide further guidance to the formulator.

EXAMPLE XI

Base mouthwash compositions comprising water, 15% ethanol, standard flavorants and dyes are prepared and blended with the following combinations of ingredients to provide mouthwash compositions A, B and C, as follows.

| Ingredient (wt. ratio) | Percent (wt.) in Mouthwash |
| --- | --- |
| A. $H_2O_2$/TDS (1:1) | 2.0 |
| B. EHDP/TMS (0.1:1) | 2.0 |
| C. STPP/TMS/CPC (10:1:0.5) | 5.0 |

As can be seen from the foregoing, a wide variety of compositions useful for treating teeth in patients who are susceptible to dental calculus formation and in need of such treatment are provided by the practice of this invention. It will also be appreciated that "multiple" compositions can be used in conjunction with each other, e.g., a toothpaste comprising TMS/TDS plus a separate toothpaste or mouthwash comprising pyrophosphate, can be separately applied to the teeth, followed by a mouthrinse using, for example, TRICLOSAN, to afford multiple benefits. Such separate usage would not depart from the spirit and scope of this invention.

What is claimed is:

1. An oral care composition comprising an effective amount of an anticalculus agent which is a member selected from the group consisting of the acid or salt form of tartrate monosuccinate, tartrate disuccinate, and mixtures thereof, and a toxicologically acceptable oral carrier.

2. An oral care composition according to claim 1 comprising at least about 0.1% by weight of said anticalculus agent.

3. An oral care composition according to claim 2 comprising from about 1% to about 15% by weight of said anticalculus agent.

4. An oral care composition according to claim 1 wherein said anticalculus agent is a mixture of said tartrate monosuccinate and tartrate disuccinate at a weight ratio of tartrate monosuccinate: tartrate disuccinate from about 20:80 to about 80:20.

5. An oral care composition according to claim 4 wherein said anticalculus agent comprises a mixture of tartrate monosuccinate and tartrate disuccinate at a weight ratio of about 40:60 of tartrate monosuccinate:-tartrate disuccinate.

6. An oral care composition according to claim 1 wherein said oral carrier is a dentifrice.

7. An oral care composition according to claim 1 wherein said oral carrier is a mouthwash.

8. An oral care composition according to claim 1 wherein said oral carrier is a lozenge, or the like.

9. An oral care composition according to claim 1 wherein said oral carrier is a chewing gum.

10. An oral care composition according to claim 1 which additionally comprises a source of an effective amount of fluoride ions.

11. An oral care composition according to claim 10 wherein said source of fluoride ions comprises from about 0.01% to about 1% by weight of said composition.

12. An oral care composition according to claim 10 in the form of a dentifrice.

13. An oral care composition according to claim 10 in the form of a mouthwash.

14. An oral care composition according to claim 1 which additionally comprises an effective amount of an antibacterial agent.

15. An oral care composition according to claim 14 wherein said antibacterial agent is 5-chloro-2-(2,4-dichlorophenoxy)phenyl.

16. An oral care composition according to claim 14 which additionally comprises a source of an effective amount of fluoride ions.

17. An oral care composition according to claim 16 wherein said antibacterial agent is 5-chloro-2-(2,4-dichlorophenoxy)phenyl.

18. An oral care composition according to claim 1 which additionally comprises an effective amount of a source of pyrophosphate ions.

19. An oral care composition according to claim 18 which additionally comprises a source of an effective amount of fluoride ions.

20. An oral care composition according to claim 18 which additionally comprises an effective amount of an antibacterial agent.

21. An oral care composition according to claim 20 wherein said antibacterial agent is 5-chloro-2-(2,4-dichlorophenoxy)phenyl.

22. An oral care composition according to claim 19 which additionally comprises an effective amount of 5-chloro-2-(2,4-dichlorophenoxy)phenyl.

23. An oral care composition according to claim 1 which additionally comprises an effective amount of zinc citrate.

24. An oral care composition according to claim 1 in the form of a dentifrice, comprising:
from about 15% to about 30% by weight of an abrasive;
from about 0.1% to about 15% by weight of an anticalculus agent which comprises a mixture of tartrate monosuccinate and tartrate disuccinate at a weight ratio of tartrate monosuccinate:tartrate disuccinate of about 40:60; and
from about 0.05% to about 0.5% by weight of a source of fluoride ions.

25. An oral care composition according to claim 1 which additionally comprises an effective amount of a source of cation selected from the group consisting of zinc, indium, strontium and stannous cations, and mixtures thereof.

26. An oral care composition according to claim 1 which additionally comprises an effective amount of a member selected from the group consisting of sodium nitrate and potassium nitrate.

27. An oral care composition according to claim 1 which additionally comprises an effective amount of a member selected from the group consisting of hydrogen peroxide, sodium tripolyphosphate, EDTA, ethane-1-hydroxy-1,1-diphosphonate, magnesium monoperphthalate, and mixtures thereof.

28. A method for preventing the accumulation of calculus on dental enamel comprising contacting said dental enamel with a safe and effective amount of tartrate monosuccinate anion, tartrate disuccinate anion, or mixtures thereof.

29. A method according to claim 28 which employs a mixture of said tartrate monosuccinate and disuccinate on a daily basis.

30. A method according to claim 28 which is carried out in conjunction with the use of a member selected from the group consisting of fluoride ions, antibacterial agents, a source of pyrophosphate ions, a metal cation selected from the group consisting of zinc, indium, strontium and stannous cations, sodium nitrate, potassium nitrate, or mixtures thereof.

31. A method according to claim 28 which is assisted by brushing said dental enamel with an abrasive.

* * * * *